United States Patent
Zupkas

[19]
[11] Patent Number: 5,935,094
[45] Date of Patent: Aug. 10, 1999

[54] PENTOSANPOLYSULFATE COATING FOR MEDICAL DEVICES

[75] Inventor: Paul F. Zupkas, San Diego, Calif.

[73] Assignee: Uros Corporation and The Regents of The University of California, San Diego, Calif.

[21] Appl. No.: 08/942,972

[22] Filed: Oct. 3, 1997

Related U.S. Application Data

[63] Continuation of application No. 08/642,391, May 3, 1996, abandoned.

[51] Int. Cl.$^6$ ...................................................... A61M 5/00
[52] U.S. Cl. ................................... 604/8; 604/4; 524/706
[58] Field of Search ..................... 604/8–10, 4; 524/706; 525/453; 528/72, 73; 523/112, 122; 427/2.1

[56] References Cited

U.S. PATENT DOCUMENTS

| | | |
|---|---|---|
| 3,617,344 | 11/1971 | Leinin et al. . |
| 4,240,163 | 12/1980 | Galin . |
| 4,326,532 | 4/1982 | Hammar . |
| 4,678,660 | 7/1987 | McGary et al. . |
| 4,720,512 | 1/1988 | Hu et al. . |
| 4,895,566 | 1/1990 | Lee . |
| 5,047,020 | 9/1991 | Hsu . |
| 5,077,052 | 12/1991 | Franzoni et al. . |
| 5,292,362 | 3/1994 | Bass et al. . |
| 5,366,505 | 11/1994 | Farber . |
| 5,436,291 | 7/1995 | Levy et al. . |
| 5,437,672 | 8/1995 | Alleyne ..................................... 606/61 |
| 5,605,938 | 2/1997 | Roufa et al. .............................. 514/59 |

FOREIGN PATENT DOCUMENTS

| | | |
|---|---|---|
| 0 080 908 | 6/1983 | European Pat. Off. . |
| 0 124 200 A2 | 11/1984 | European Pat. Off. . |
| WO 93/03776 | 3/1993 | WIPO . |

*Primary Examiner*—John G. Weiss
*Assistant Examiner*—Ki Yong
*Attorney, Agent, or Firm*—Knobbe, Martens, Olson & Bear, LLP

[57] ABSTRACT

A pentosanpolysulfate coating on medical devices reduces or eliminates side effects associated with the introduction of foreign bodies into the urinary tract of a patient. The pentosanpolysulfate coating attenuates the attachment of salts, minerals, proteins, salt, and other undesirable materials onto the medical device used in the urinary tract. Inflammatory or foreign body reaction to these pentosanpolysulfate coated medical devices are also attenuated, and growth of healthy normal tissue in the vicinity of the coated medical device of the present invention is allowed.

20 Claims, 1 Drawing Sheet

PENTOSANPOLYSULFATE COATING FOR MEDICAL DEVICES

This application is a continuation of U.S. patent application Ser. No. 08/642,391, filed May 3, 1996 now abandoned.

BACKGROUND OF THE INVENTION

Field of the Invention

The present invention relates generally to medical devices and, more particularly, to medical device coatings for increasing the biocompatibility of the medical device.

Description of Related Art

Biocompatibility is a measure of the response of the interaction of a material to tissues or biological fluids. A material is said to be biocompatible if it is accepted by tissue and causes no adverse reaction or response by the body. Biocompatibility is particularly important in medical devices where long term contact between the device and the patient is required. The use of surface coatings to improve the biocompatibility of medical devices is well known in the art. Surfaces of medical devices can be modified to reduce erosion, mechanical failure, migration, inflammatory response, thrombosis, or other complications associated with the interaction between patient and device. The coatings of medical devices have applications in all areas of medicine, but are particularly important in combination with the use of prosthetic devices designed for permanent or long dwelling patient implantation. The coatings of medical devices have played a particularly important role in the design of medical devices for use in the urinary tract.

Devices in the urinary tract are exposed to both urine and the cells lining the inside of the urinary tract, the transitional epithelium or urothelium. The urinary tract also contains a layer of smooth muscle that provides the driving force, with other tissues and organs, for the transport of urine through the urinary tract and out of the body, a process described as micturition. Urine is filtered from the blood in the kidneys. It is transported from the kidneys to the bladder via the ureters. Ureters are conduits that transport the urine in boli in a peristaltic function under normal conditions. The urine collects in the bladder until it is voided via the urethra. Sphincters at the bladder neck and in the urethra play an important role in the voluntary control of micturition.

Disease or trauma can adversely effect the function of the urinary tract. Such conditions cause pain and can lead to death if left untreated. U.S. Pat. No. 5,180,715 to Parsons et al. discusses the benefits of pentosanpolysulfate for the treatment of chronic bladder infections, interstitial cystitis, bladder tumors, and other disorders of the bladder. Parsons describes benefits of pentosanpolysulfate in affecting the glucoaminoglycan (GAG) layer lining the inner bladder wall by irrigating the bladder with the drug, or by the systemic delivery of the drug by oral administration. Parsons discloses that the adherence of bacteria to the bladder wall after removal of the GAG layer is markedly reduced by exposing the wall to pentosanpolysulfate. U.S. Pat. Nos. 4,966,980 and 4,280,693 both to Gillespie describe the benefits of sodium pentosanpolysulfate in arresting the process of angiogenesis or the growth of new capillary blood vessels. This process is central to the growth of tumors and the progression of the inflammatory and immune responses. In combination with angiostatic steroids to improve the transport of the pentosanpolysulfate, Gillespie describes the benefits of pentosanpolysulfate to treat interstitial cystitis, tumors, and angiosarcomas.

Medical devices are frequently used to either treat conditions or to substitute functions of organs in the urinary tract. Common urinary devices include (1) ureteral stents for treating obstruction of the ureter, ureteric fistulas, and gaps or defects caused by trauma or other conditions, (2) urethral catheters for treating benign prostate growth, urethral strictures, and incontinence, (3) incontinence devices for treating the lack of control of micturition, and (4) penile prosthetics for treating erectile dysfunction. These devices often must function in the urinary tract for extended periods of time. Factors to be considered in choosing medical device materials for use in the urinary tract or urodevices include the effect of the urodevice on the urothelium, infection and bacteria growth, and encrustation and stone formation.

Prolonged contact of urodevices with the urothelium has led to ulceration, inflammatory response, smooth muscle atrophy, and fibroplasia. Two primary factors which help to determine the response of the urothelium in contact with urodevices are the exposure time and the material properties of the urodevice. A wealth of literature exists on the biocompatibility of materials on the urothelium. Latex has been shown to have a harmful effect on the urothelium, causing an inflammatory response and hyperplasia. Silicone, while much less toxic than latex, has been observed to cause stone formation and mucus metaplasia. Other polymers, such as polyurethanes, have a similar effect on the urothelium. One property that appears to have a dramatic effect on the biocompatibility of a material in the urinary tract is the attraction of water to the material. Materials that attract water, or hydrophilic materials, are much more biocompatible than materials that repel water, or hydrophobic materials. The greater biocompatibility of hydrophilic materials is partially why hydrogel coatings of urodevices dramatically increases their biocompatibility. A number of patents, U.S. Pat. Nos. 5,401,508, 5,295,978, 5,453,467, and 5,468,787, describe designs, benefits, and functions of urodevices that utilize hydro-gel and other hydrophilic polymeric coatings.

The adherence of bacteria to the surfaces of urodevices may initiate a process that leads to infection. The exact relationship between the formation of bacteria on the surface of urodevices and the appearance of infection symptoms, however, is not clearly understood. Bacteria adhere to surfaces using a mucopolysaccharide, gradually forming a biofilm on the surface of the urodevice. The bacteria in this biofilm are resistant to antibiotic therapy. Thus, treatment of infection can resolve clinical symptoms, but the source of the infection may still remain intact. In various studies of the adherence of bacteria to various urodevice materials the bacteria adhered to every tested material.

Encrustation and stone formation are one of the major failure modes of long term indwelling urodevices. Encrustation can occlude lumens, block orifices, and completely encase urodevices in the urinary tract. One process of encrustation and stone formation results from the presence of urease secreting bacteria in the urinary tract, causing the urine to become alkaline. The alkalinity of the urine causes precipitation of minerals (primarily struvite and calcium oxalate). These minerals precipitate on foreign bodies in the urinary tract leading to encrustation, or on themselves leading to stone formation. However, the process of encrustation and stone formation can occur regardless of the presence of bacteria, being idiopathic, related to the stone forming ability of the patient, or to a primary metabolic disorder. Although rates of stone formation and encrustation may differ, it appears that all materials placed in the urinary tract will eventually become encrusted or cause stone formation.

A basic prior art approach for improving the function and efficacy of medical devices is to coat the device surface with a thin layer of polymers, biomolecules, or other materials that enhance the biocompatibility of the base or the substrate material forming the bulk of the device. Coatings have played an important role in improving the biocompatibility of medical devices that are exposed to body tissue and fluids. Coatings have been used to reduce formation of blood clots or thrombosis, bacterial adherence, stone formation and encrustation, adverse tissue reactions, and trauma caused by physical interaction between device and body tissues. Coatings used on medical devices include hydrophilic polymers or hydrogels, heparin, albumin, hyaluronic acid, fibronectin, enzymes, amino acids, growth hormones, and other bioactive materials as disclosed in U.S. Pat. Nos. 5,451,424, 5,324,647, 5,308,641, and 5,023,114. Heparin coating is well recognized to enhance the biocompatibility of medical devices, as disclosed in U.S. Pat. Nos. 4,613,517 and 4,329,383, but the anticoagulative properties and reduction in bioreactivity after surface attachment of heparin have limited its usefulness as a coating for long-term implantable medical devices.

Numerous processes exist for altering the surface of a medical device to promote the coating of material on the device surface. These processes include (1) plasma treatment with high energy gases at low temperatures altering the surface chemistry of the bulk material, creating free radical binding sites on the surface, or creating a surface deposition by the polymerization of the surface with the plasma gas free radicals, as disclosed in U.S. Pat. No. 4,613,517; (2) photochemical immobilization of a biomolecule on the polymer surface by attaching a photoreactive group to the biomolecule followed by application and photolysis of the biomolecule to the polymer surface, as disclosed in U.S. Pat. Nos. 5,258,041 and 5,002,582; and (3) gamma or electron beam-irradiation of a polymer surface in contact with a solution containing a monomer that is then polymerized on the surface of the base polymer, as disclosed in U.S. Pat. Nos. 5,094,876 and 4,806,302. Additional well-known methods of attaching biomolecules or coating materials onto the surfaces of polymers also exist in the prior art.

SUMMARY OF THE INVENTION

The pentosanpolysulfate coating of the present invention reduces or eliminates side effects associated with the introduction of foreign bodies into the urinary tract of a patient. The pentosanpolysulfate coating attenuates the attachment of minerals, proteins, salts, and other undesirable materials onto the medical device used in the urinary tract. Inflammatory or foreign body reaction to the pentosanpolysulfate coated medical devices of the present invention are also attenuated, while growth of healthy normal tissue in the vicinity of the coated medical device of the present invention is maintained.

According to the present invention, a mucopolysaccharide, sodium pentosanpolysulfate is coated onto a surface of a medical device using any of the above-mentioned coating processes. The layer of pentosanpolysulfate enhances the biocompatibility of the medical device, thus reducing adverse reactions between the medical device and biological fluids and tissues.

The present invention recognizes that pentosanpolysulfate is a highly sulfated and hydrophilic compound. Pentosanpolysulfate has been recognized in the prior art as a mild anticoagulant and a compound having major benefits in the treatment of urinary disorders by affecting the mucous and glucoaminoglycan (GAG) layer that lines the inside of the urinary tract. Pentosanpolysulfate is one of many drugs in a family of mucopolysaccharides, having an ability to affect the clotting mechanisms of blood. Heparin is a well recognized drug in this class. Although pentosanpolysulfate and heparin possess similar properties, pentosanpolysulfate is more homogeneous in its molecular weight and the distribution of its negatively charged active sulfate radical groups. Thus, although pentosanpolysulfate has been a drug having known treatment properties for blood coagulation, urinary tract disorders, and other conditions, the prior art has not provided a layer of pentosanpolysulfate on medical devices, as does the present invention.

According to one feature of the present invention, a medical device having a layer of pentosanpolysulfate is adapted for use in a urinary tract. The medical device includes a polymeric material produced by one of an extrusion process, a molding process, and a dipping process. The medical device may be a ureteral stent, an artificial bladder, an artificial sphincter, or an artificial bladder patch.

According to another feature of the present invention, a synthetic bladder patch for providing pressure relief to spontaneous contractions of a bladder and for enlarging the bladder to increase a volume of the bladder is provided. The synthetic bladder patch includes an artificial material and a layer of pentosanpolysulfate over the artificial material. The layer of pentosanpolysulfate allows the synthetic bladder patch to be grafted on a bladder and attenuates the problems associated with encrustation, infection, and inflamatory response.

According to another feature of the present invention, a non-dissolvable suture for permanently attaching a device in a urinary tract of a patient is provided. The non-dissolvable suture includes a base material and a layer of pentosanpolysulfate disposed over the base material. The layer of pentosanpolysulfate makes the non-dissolvable suture adaptable for permanently suturing a device within the urinary tract of the patient.

According to another feature of the present invention, a ureteral stent for substituting the function of the ureter as a conduit for the passage of urine from kidneys to a bladder for extended periods of time is provided. The ureteral stent includes a polymeric base material forming a tube with an inner surface and an outer surface, and further includes a layer of pentosanpolysulfate disposed over both the inner surface and the outer surface of the polymeric base material. The layer of pentosanpolysulfate might extend the time the ureteral stent remains within the patient for a period in excess of six months.

According to one method of the present invention, a surface of a medical device is coated with a layer of pentosanpolysulfate by first providing an attachment area on the surface of the medical device and, subsequently, exposing the surface of the medical device to a solution comprising sodium pentosanpolysulfate, to thereby coat the attachment area with a layer of pentosanpolysulfate. An additional step of removing at least one byproduct or residual from the surface of the medical device leaves only the attachment area coated with the layer of pentosanpolysulfate. The step of providing an attachment area may include a step of attaching a secondary molecular surface to the attachment area and a step of creating the attachment area on the secondary molecular surface, wherein the attachment area is suitable for binding pentosanpolysulfate molecules thereto. The solution having pentosanpolysulfate may also include an attaching agent, which may include carrier molecules.

The step of creating the attachment area may include a step of exposing the surface of the medical device to a solution containing an agent with a low pH, or may include a step of exposing the surface of the medical device to a solution of photoreactive agents and a high electromagnetic energy source. Alternatively, the attachment area creation may include a step of exposing the surface of the medical device to high energy plasma or a high energy radiation, which may comprise gamma or corona discharge.

The present invention, together with additional features and advantages thereof, may best be understood by reference to the following description taken in connection with the accompanying illustrative drawing.

DETAILED DESCRIPTION OF THE PRESENTLY PREFERRED EMBODIMENTS

Figure 1:
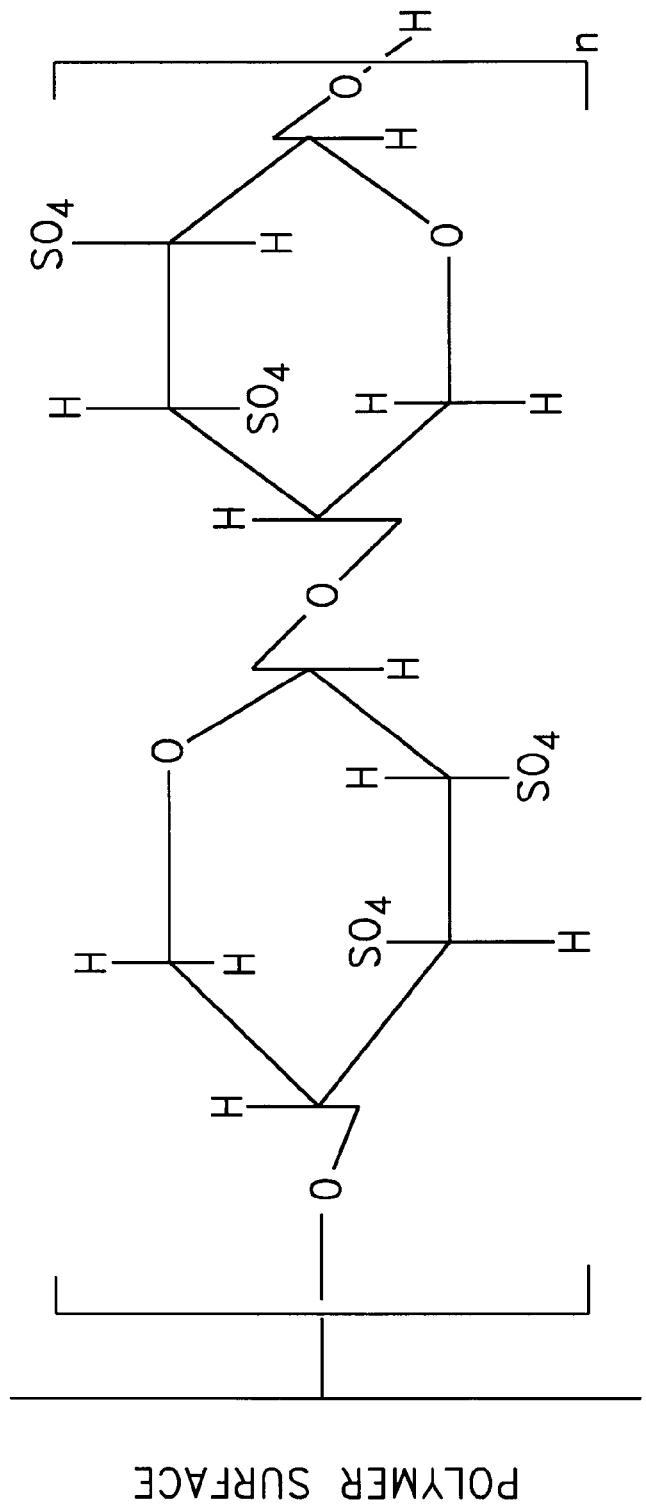
FIG. 1 illustrates a repeating pentosanpolysulfate chain attached to a polymer surface of a medical device, according to the presently preferred embodiment.

Although pentosanpolysulfate has been recognized as a drug for treating urinary tract conditions, pentosanpolysulfate has not been utilized as a material for coating medical devices, until the present invention. It has been discovered that medical devices coated with pentosanpolysulfate have enhanced biocompatibility.

In the presently preferred embodiment, the medical devices are formed of polymers, such as silicone polysiloxane, polyurethane polypropylene, polyethylene, polytetrafluorethylene, polyvinylchloride or polycarbonate. Other polymers may be used, or, alternatively, other materials besides polymers may be used with the present invention. Any conventional coating process may be used to attach the pentosanpolysulfate to the surface of the medical device. The basic requirement for the coating process is to provide an attachment area on the surface of the medical device for the bonding of the pentosanpolysulfate chains. These bonds may be either ionic or covalent. According to the presently preferred embodiment, covalent bonds are preferred over ionic bonds, since covalent bonds provide stronger attachment between the pentosanpolysulfate and the medical device surface.

FIG. 1 illustrates a commercially available sodium salt form of the pentosanpolysulfate compound used in the presently preferred embodiment, attached to a polymer surface. The molecular weight of the molecule is determined by the number of repeating pentosanpolysulfate chains. The optimal molecular weight for pentosanpolysulfate is 2000.

An empirical study using rabbits as specimens demonstrates the benefits of the presently embodied pentosanpolysulfate coating on materials to enhance the biocompatibility of the materials. In this study, sections of 0.025 inch thick silicone (polysiloxane) sheet material coated with pentosanpolysulfate and non-coated sheet material were implanted in the bladders of New Zealand White rabbits in the weight range 2.5 to 3.0 kilograms. One group of ten rabbits received the pentosanpolysulfate coated material, while the other received the non-coated material. The generic silicone material was coated using a photochemical immobilization process, whereby pentosanpolysulfate was covalently bonded to the silicone surface. The presence of the pentosanpolysulfate coating on the surface of the silicone sheet was confirmed by the staining of the coated material with Toluidine Blue dye. The surgical preparation and procedure was the same for both groups of rabbits. The rabbits were anesthetized using intramuscular injections of a 70/30 combination of Ketaset (ketamine chloride) and Anaset (xylazine). All rabbits' bladders were catheterized with a 5 Fr pediatric feeding tube to drain the bladder of urine. A midline abdominal incision of approximately 2.5 centimeters was made to expose the bladder. A small incision was made in the apex of the superior surface of the rabbit bladders. Two groups of ten gas sterilized sections of silicone sheet material, one coated and another non-coated, approximately 3 centimeters by 1.5 centimeters, were placed in the rabbit bladders. All sections of silicone were anchored to the inner surface of the bladder apex with a single 5-0 Dexon suture. The bladders were closed with 5-0 Dexon sutures and the abdominal incisions were closed with running 3-0 sutures. All rabbits were given intramuscular injections of Baytril (Enrofloxacin), a broad spectrum anti-biotic, at the conclusion of the surgery.

All rabbits were maintained on standard rabbit pellet chow and water for ten weeks. Daily intramuscular injections of Baytril were given to all rabbits for the first week after surgery. The rabbits were monitored daily and weighed weekly. Two rabbits in the uncoated silicone group were noted to be dehydrated during the third week and were given subcutaneous fluid injections. Subsequent worsening of their physical conditions and hematuria led to both animals being euthanized with intravascular injections of Beuthanunal before the end of their third postoperative week. Examination of the euthanized rabbit bladders at autopsy revealed both bladders to be ulcerated and silicone sections encrusted with a hard yellow material determined to contain significant amounts of calcium phosphate. All of the remaining rabbits (ten in the coated silicone group and eight in the uncoated silicone group) progressed without event for the ten week postoperative period.

At the end of the tenth postoperative week, all of the rabbits were sacrificed with intravascular injections of Beuthanizing fluid. All of the bladders were examined at autopsy. In the uncoated silicone group, the silicone was completely encrusted in a hard yellow material determined to consist mainly of calcium phosphate. The bladder surface of all rabbits in the uncoated silicone group exhibited some degree of disruption varying from a mid-inflammatory reaction to major ulcerations of the bladder surface. In the coated silicone group, the silicone sections in seven rabbits were completely free of any encrustation. In the remaining three rabbits in the coated silicone group, small stone formations were observed at the sites where the anchoring sutures had been placed through the silicone sections. In one case, the silicone section was attached to the bladder wall by the stone, and the stone shape resembled the shape of the suture, implying that encrustation occurred around the suture before it could dissolve. All of the bladder surfaces, with the exception of the stone attachment, appeared normal and healthy. Staining of all coated silicone sections with Toludiene Blue showed the same level of coating of pentosanpolysulfate on the surface of the implanted silicone as on the coated silicone sections before the implant.

The use of the pentosanpolysulfate coating in the above study reduced encrustation and adverse tissue reactions, which are typically associated with foreign bodies in the urinary tract of a patient. Although studies have examined the use of a variety of coatings to enhance biocompatibility, no study has identified the benefits of pentosanpolysulfate as a coating material.

The use of pentosanpolysulfate as a coating material for medical devices, according to the present invention, allows for new medical devices and applications of existing medical devices which have not been possible previously in the prior art. Many medical devices of the prior art were plagued with problems associated with the interactions of body tissues and fluids with the medical devices. Medical devices, which can be coated with the pentosanpolysulfate layer include ureteral stents adapted for substituting a normal function of a ureter and providing a conduit for urine between the bladder and the kidney, artificial bladders adapted for collecting urine to substitute a normal function of a bladder, artificial sphincters adapted for providing a means of continence, and bladder patches adapted for grafting onto the bladder to increase a volume of the bladder and to provide a pressure relief for both undesirable contractions of the bladder and concurrent pressure increases associated with the contractions.

Another embodiment of the present invention is a synthetic bladder patch, which can be placed in the bladder wall to provide a pressure relief from the spontaneous contraction of the bladder or for enlarging the bladder to increase bladder volume. Conventional bladder patches have been used in the treatment of diseases such as interstitial cystitis and chronic bladder infections where the gradual atrophy of the bladder wall reduces bladder filling capacity. One method of creating a bladder patch involves the removal and grafting of tissue from other organs, such as the bowel, into the bladder wall. These conventional grafting procedures have met with limited success.

Diseases such as neurogenic bladder and urinary urge incontinence involve the spontaneous contraction of the bladder causing urine leakage. One method for treating these disorders involves the removal of the smooth muscle layer from one section of the bladder to create a "thin walled blowout patch." Although this conventional treatment can reduce urine leakage, regrowth of the thinned section often returns the patient to the original state. The synthetic bladder patch of the present invention does not require stripping of delicate tissue from the bladder wall, but can serve substantially the same function as the blowout patch. The pentosanpolysulfate coating of the bladder patch allows the patch to be permanently placed into the bladder wall.

Another embodiment of the present invention is a non-dissolvable suture for use in the urinary tract to permanently anchor or attach devices within the urinary tract. Conventional sutures are used in the urinary tract, but these sutures are typically dissolvable in nature. Depending upon the material, dissolvable sutures of the prior art dissolve in as little as 8 to 10 days. These conventional dissolvable sutures reduce the encrustation and inflammatory response of the suture but, obviously, are not permanent. The non-dissolvable, pentosanpolysulfate sutures of the present invention reduce or eliminate the encrustation and inflammatory response problem associated with conventional sutures, and can thus be permanently installed within the urinary tract, to thereby permanently suture a device within the urinary tract.

The pentosanpolysulfate coating of the present invention may also be used for providing cardiovascular stents or ureteral stents. The coated ureteral stents, for example, according to the present invention, substitute the function of the ureter as a conduit for the passage of urine from the kidneys to the bladder for extended periods of time. Conventional ureteral stents have been used to treat ureteral obstruction, fistulas, and wall defects, and have been made of a variety of polymeric materials with a host of mechanical and biocompatibility characteristics. These conventional ureteral stents have been coated with materials, such as hydrogel, which facilitate sliding of the ureteral stent over guidewires. These conventional ureteral stents may be placed for periods of time varying from 2 weeks to 6 months. The installation periods of these conventional ureteral stents, however, are often limited by particular reactions of the patient, with no clear determining factors. The ureteral stent of the present invention, however, comprises a pentosanpolysulfate coating that reduces the infection and encrustation associated with conventional uncoated stents. This makes the ureteral stent of the present invention capable of being disposed within the urinary tract for longer periods than uncoated stents and possibly for periods in excess of 6 months.

The base portion of the ureteral stent preferably comprises a polymeric material, such as a polyurethane, polyethylene, or polypropylene capable of maintaining the integrity of a conduit. The ureteral stent of the present invention preferably comprises an internal diameter large enough to allow the free flow of urine, and an external diameter small enough to allow passage and positioning of the stent within the ureter or other organs. The pentosanpolysulfate coating of the ureteral stent of the present invention covers the lumen (interior surface) of the ureteral stent to thereby prevent encrustation which would eventually lead to blockage of the urine flow by the formation of stones, and also coats the external surface of the ureteral stent to thereby improve the interaction between the ureteral stent and the urothelium of the outer wall. The ureteral stent of the present invention, coated with pentosanpolysulfate, is capable of remaining in place within a urinary tract of a patient for longer periods of time than comparable conventional devices with fewer complications.

Although exemplary embodiments of the invention have been shown and described, many other changes, modifications and substitutions, in addition to those set forth in the above paragraphs, may be made by one having ordinary skill in the art without necessarily departing from the spirit and scope of this invention.

I claim:

1. A medical device comprising a body with a surface, wherein said surface is modified by a process which alters the chemical nature thereof so as to generate or attach reactive chemical groups on an area of said surface that enhance bonding of pentosanpolysulfate thereon, and a layer of pentosanpolysulfate bonded on said area of said surface by means of said reactive chemical groups.

2. The medical device recited in claim 1, wherein said surface comprises a polymeric material produced by one of an extrusion process, a molding process, and a dipping process, wherein the medical device is selected from the group consisting of a ureteral stent and an artificial bladder.

3. The medical device as recited in claim 1, the layer of pentosanpolysulfate being permanently bonded to the surface of the medical device.

4. The medical device as recited in claim 1, the layer of pentosanpolysulfate being covalently bonded to the surface of said medical device.

5. The medical device as recited in claim 1, the layer of pentosanpolysulfate being ionically bonded to the surface of the medical device.

6. The medical device s recited in claim 1, wherein the layer of pentosanpolysulfate remains on the surface when the medical device is implanted into a patient.

7. The medical device of claim 1, wherein said reactive chemical groups are generated or attached by a method selected from the group consisting of exposing said medical device to a solution of photoreactive agents and a high electromagnetic energy source and exposing the surface of the medical device to a high energy plasma or high energy radiation.

8. The medical device of claim 1, wherein said attachment area comprises a secondary molecular structure attached thereto.

9. The medical device of claim 1, wherein the entire surface of said medical device is covered by said pentosanpolysulfate.

10. The medical device of claim 1, wherein said pentosanpolysulfate forms a layer on said surface.

11. The medical device of claim 1, wherein said pentosanpolysulfate is present in an amount effective to attenuate attachment of materials present in the urinary tract to said surface.

12. A medical device, comprising:
    a synthetic bladder patch for providing pressure relief to spontaneous contractions of a bladder and for enlarging the bladder to increase a volume of the bladder, the synthetic bladder patch comprising:
        an artificial material forming a surface of the synthetic bladder patch wherein said surface is modified by a process which alters the chemical nature thereof so as to generate or attach reactive chemical groups on an area of said surface that enhance binding of pentosanpolysulfate thereto; and
        pentosanpolysulfate bonded on said area of said surface by means of said reactive chemical groups.

13. The synthetic bladder as recited in claim 12, the layer of pentosanpolysulfate being permanently bonded to the surface of the synthetic bladder patch.

14. A medical device, comprising:
    a ureteral stent for substituting the function of the ureter as a conduit for the passage of urine from kidneys to a bladder for extended periods of time, the ureteral stent comprising:
        a polymeric base material forming a tube with an inner surface and an outer surface; and
        a layer of pentosanpolysulfate bonded to portions of the polymeric base material which may be exposed to urine.

15. The ureteral stent as recited in claim 14, the layer of pentosanpolysulfate being permanently bonded to both the inner surface and the outer surface.

16. The ureteral stent of claim 14, wherein the layer of pentosanpolysulfate remains over both the inner surface and the outer surface thereof after implantation into a patient.

17. A medical device, comprising:
    a body with a contacting surface for contacting at least one of a body tissue and a body fluid, wherein said surface is modified by a process which alters the chemical nature thereof so as to generate or attach reactive chemical groups on an area of said surface that enhance bonding of pentosanpolysulfate thereto; and
    a layer of pentosanpolysulfate bonded on said attachment area of the contacting surface by means of said reactive chemical groups.

18. The medical device as recited in claim 17, the layer of pentosanpolysulfate being covalently bonded to the surface of the medical device.

19. The medical device as recited in claim 17, the layer of pentosanpolysulfate being ionically bonded to the surface of the medical device.

20. The medical device as recited in claim 17, the layer of pentosanpolysulfate being permanently bonded to the surface of the medical device.

* * * * *